Figure 1:
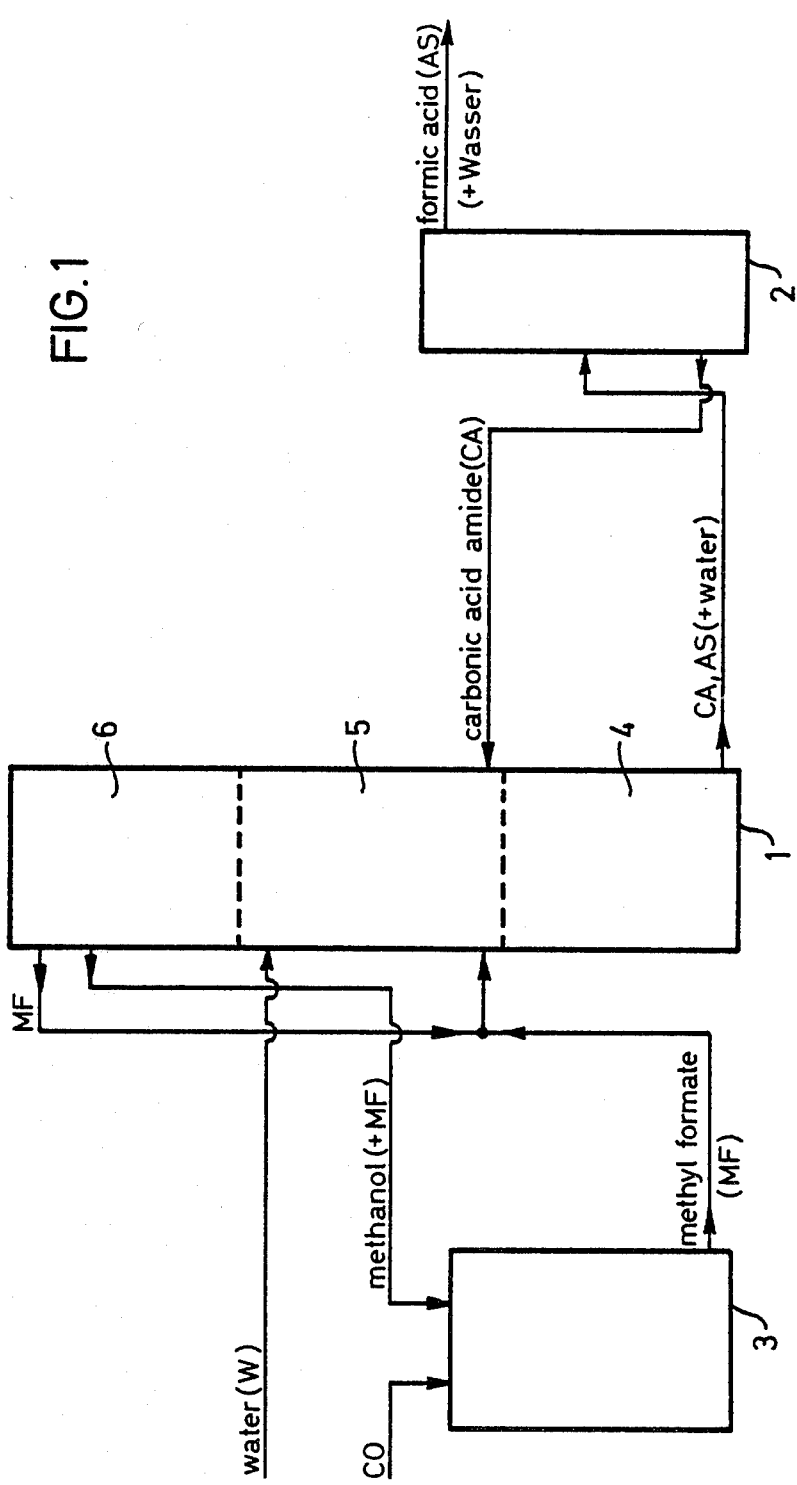

United States Patent [19]

Bott et al.

[11] 4,262,140
[45] Apr. 14, 1981

[54] PRODUCTION OF ANHYDROUS OR SUBSTANTIALLY ANHYDROUS FORMIC ACID

[75] Inventors: Kaspar Bott, Wachenheim; Gerd Kaibel, Lampertheim; Herwig Hoffmann, Frankenthal; Otto Kratzer, Bobenheim-Roxheim; Rudolf Irnich, Bobenheim, all of Fed. Rep. of Germany

[73] Assignee: BASF Aktiengesellschaft, Fed. Rep. of Germany

[21] Appl. No.: 99,760

[22] Filed: Dec. 3, 1979

[30] Foreign Application Priority Data

Dec. 14, 1978 [DE] Fed. Rep. of Germany ....... 2853991

[51] Int. Cl.³ .............................................. B01D 3/34
[52] U.S. Cl. .................................... 562/609; 203/15; 203/28; 203/43; 203/50
[58] Field of Search ................. 203/15, 28, 39, 42–46, 203/59, 57; 562/609, 606

[56] References Cited

U.S. PATENT DOCUMENTS

4,143,066  3/1979  Kalcevic ................................ 203/43

FOREIGN PATENT DOCUMENTS

2407157  8/1976  Fed. Rep. of Germany ........... 562/609
2545658  4/1977  Fed. Rep. of Germany ........... 562/609
2545730  4/1977  Fed. Rep. of Germany ........... 562/609
2744313  9/1978  Fed. Rep. of Germany ........... 562/609

OTHER PUBLICATIONS

Enzykopädie der Technischen Chemie, 4th ed., vol. 7, pp. 365–366.

*Primary Examiner*—Frank Sever
*Attorney, Agent, or Firm*—Keil & Witherspoon

[57] ABSTRACT

A process for the production of anhydrous or substantially anhydrous formic acid by hydrolysis of methyl formate which is carried out in a column having an upper fractionating section, a middle hydrolysis section and a lower extraction section and in which (a) the hydrolysis is carried out in the middle section of the columm, with water and methyl formate in countercurrent, (b) the resulting formic acid is extracted, in the lower section of the column, by means of a carboxylic acid amide which is fed into the lower end of the middle section of the column, (c) the extract phase, consisting in the main of formic acid and the carboxylic acid amide, is distillatively dehydrated, or substantially dehydrated, in the lower section of the column, (d) the methanol and uncovered methyl formate are removed by fractional distillation in the upper section of the column and (e) the pure formic acid or concentrated aqueous formic acid is distilled from the anhydrous or substantially anhydrous extract phase in a second column, leaving the carboxylic acid amide.

5 Claims, 2 Drawing Figures

PRODUCTION OF ANHYDROUS OR SUBSTANTIALLY ANHYDROUS FORMIC ACID

The present invention relates to a novel process for the production of anhydrous or substantially anhydrous formic acid by hydrolysis of methyl formate.

"Ullmanns Enzyklopädie der Technischen Chemie", 4th edition, Volume 7, page 365, discloses the preparation of formic acid by acidolysis of formamide with sulfuric acid. This process, which is operated industrially, however has the disadvantage that it necessarily also produces stoichiometric amounts of ammonium sulfate.

In spite of this disadvantage, the hydrolysis of methyl formate $$HCOOCH_3 + H_2O \rightleftharpoons HCOOH + CH_3OH$$

which is also known (Ullmann, loc. cit., page 366), and which at first sight appears substantially more advantageous, has hitherto not found acceptance in industry, in the main because of the high rate at which re-esterification occurs, due to formic acid, being a strong acid, acting as a catalyst. It is true that the re-esterification can be substantially suppressed by using the special distillation process of German Pat. No. 2,407,157, but this process requires from about 7 to 8 tonnes of steam per tonne of formic acid, so that, for this reason alone, it is economically virtually ruled out. Furthermore, the process only gives a formic acid/water azeotrope, ie. an acid of only about 75% strength by weight, for which there is little demand compared to the demand for pure or highly concentrated acid.

Further, it is known from German Laid-Open Application DOS No. 2,744,313 to carry out the hydrolysis of methyl formate in the presence of about stoichiometric amounts of a base, for example 1-n-pentylimidazole. This results in an adduct of the base and formic acid, from which the remaining reactants (methyl formate, methanol and water) can easily be separated by distillation, after which the anhydrous or substantially anhydrous formic acid is distilled from the adduct in a further process step. Since the adduct is relatively stable, its cleavage requires relatively severe distillation conditions. If higher temperatures are used for this purpose, undesirable decomposition products form, which, even in traces, decolorize the formic acid, whilst if the cleavage is carried out under greatly reduced pressure, the distillation takes place too slowly.

Further, German Laid-Open Application DOS No. 2,545,658 discloses extracting carboxylic acids, including formic acid, from their aqueous solutions by means of carboxylic acid amides, eg. N-di-n-butylformamide, and then isolating the acid from the extract phase by distillation. However, such an extraction is a liquid-liquid extraction, which is preferably carried out at a relatively low temperature and which therefore, because of requiring intermediate cooling, cannot be fitted harmoniously into an overall process for the preparation of formic acid by hydrolysis of methyl formate.

Finally, in the process of German Laid-Open Application DOS No. 2,545,730 formic acid is obtained from its aqueous solutions by extractive distillation with N-formylmorpholine followed by separation of the extract phase, by distillation, into formic acid and the extractant. Since, in this process, water and formic acid must be evaporated, the process is again unsuitable for the economical production of formic acid from methyl formate.

It is an object of the present invention to produce anhydrous or substantially anhydrous formic acid from methyl formate by a method which is, overall, satisfactory for industrial operation.

We have found that this object is achieved and that anhydrous or substantially anhydrous formic acid is obtained by hydrolysis of methyl formate if the process is carried out in a column and (a) the hydrolysis is carried out in the middle section of the column, with water and methyl formate in countercurrent, (b) the resulting formic acid is extracted, in the lower section of the column, by means of a carboxylic acid amide of the general formula I

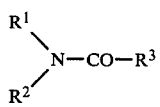

where $R^1$ and $R^2$ are alkyl, which may also be linked to form a 5-membered or 6-membered ring, or are cyclohexyl, and $R^3$ is hydrogen or $C_1$-$C_4$-alkyl, the sum of the carbon atoms in radicals $R^1$, $R^2$ and $R^3$ being from 7 to 14, the carboxylic acid amide being fed into the lower end of the middle section of the column, (c) the extract phase, consisting in the main of formic acid and the carboxylic acid amide, is distillatively dehydrated, or substantially dehydrated, in the lower section of the column, (d) the methanol and unconverted methyl formate are removed by fractional distillation in the upper section of the column and (e) the pure formic acid or concentrated aqueous formic acid is distilled from the anhydrous or substantially anhydrous extract phase in a second column, leaving the carboxylic acid amide.

A particularly advantageous and energy-saving embodiment of the process comprises an additional step (f) in which the aqueous formic acid collecting in liquid form in the lower zone of the middle section of the column below the methyl formate feed point is completely or largely withdrawn and supplied to a separate extraction column in which it is partly dehydrated by means of carboxylic acid amide I by the method of liquid-liquid extraction, the water thus obtained as the raffinate phase is advantageously returned to the upper zone of the middle section of the column, and the extract phase comprising the formic acid, the extractant and some of the water supplied to the extraction column is returned to the lower zone of the middle section of the column below the outlet for aqueous formic acid.

The attached drawing illustrates both embodiments as parts of the total process of synthesis of formic acid.

As may be seen from FIG. 1, the basic process according to the invention, which is identified by features (a) to (e) and comprises the combined hydrolysis/extraction/fractionation column (1) and the formic acid column (2) forms, together with the synthesis of methyl formate in reactor (3), a closed system into which only water and carbon monoxide are introduced and from which only pure or highly concentrated formic acid is taken off. Of course, there is also some consumption of methanol and carboxylic acid amide I, and small amounts of residue also form in the formic acid column, but this can be left out of account, since it does not affect the principle of the process.

The central apparatus of the process is the combined hydrolysis/extraction/fractionation column (1). This column consists, in accordance with the functions it performs, of the lower section (4, hereafter referred to as the extraction section), the middle section (5, referred to as the hydrolysis section) and the upper section (6, referred to as the fractionation section).

Preferably, the column is operated under atmospheric pressure, and the conditions are chosen so that the temperature is 150°–175° C. at the column bottom, 90°–105° C. at the lower end of the hydrolysis section, 75°–90° C. at the upper end of the hydrolysis section and 31°–35° C. at the top. If the column is operated under reduced pressure (down to about 700 mbar) or under superatmospheric pressure (up to about 1.5 bar), these temperatures alter in accordance with the known laws.

To carry out process step (a), namely the hydrolysis in counter-current, the water is passed into the upper zone of the hydrolysis section and the methyl formate into the lower zone of the hydrolysis section of the column. The construction of the hydrolysis section (5) of the column should be such as to provide the residence time required for the hydrolysis, which is about 1–30 minutes.

Theoretically, 1 tray would suffice in the hydrolysis section, but this would give an equilibrium which would be in favor of formic acid only to an unsatisfactory degree. This equilibrium becomes more satisfactory with increasing number of trays, in accordance with the law of mass action, as is generally known, but there are both technical and economic limits to such an increase. The process gives satisfactory results with as few as 6 trays, whilst using more than 20 trays produces no further significant advantage. Hence, the use of from 8 to 15 trays is preferred.

Since the hydrolysis section of the column is intended to maintain a defined residence time, the trays are preferably of the bubble-cap type, but the specific construction of this type of tray, of which numerous embodiments are used industrially, is immaterial. However, amongst these constructions, those which permit a high level of liquid above the tray bottom are to be recommended particularly. The process also gives good results with valve trays. Perforated trays can also be used, particularly in substantial numbers, but are in general less suitable.

If it is desired to produce anhydrous formic acid, water and methyl formate in the molar ratio of from about 0.90:1 to 0.95:1 are fed to the reaction. The excess methyl formate is needed because part of the methyl formate always passes into the lateral take-off for methanol and is thus withdrawn from the reaction. If aqueous formic acid is required, the amount of water used is increased accordingly. However, for hydrolysis under steady-state operation, the conditions chosen are such that the molar ratio of water to methyl formate in the hydrolysis section is from 30:1 to 100:1, ie. at the start of the reaction an appropriate excess amount of water must first be introduced in order to fill the hydrolysis section. Because formic acid, which is a strong acid, is formed, the hydrolysis takes place autocatalytically, but catalytic amounts of a strong acid such as p-toluenesulfonic acid or sulfuric acid may also be used. The higher rate of hydrolysis achievable by such additives must be weighed against the disadvantage that these acids react with the carboxylic acid amide I, so that losses of I, or at least regeneration costs, have to be accepted.

The fractionation section (6), located above the hydrolysis section (5), in accordance with feature (d) of the process, serves to separate methanol and methyl formate by fractionation, the methanol being substantially separated off as a liquid stream taken off at the side, whilst methyl formate is taken off as vapor or liquid at the top of the column. With 15 or more theoretical plates, it is possible to separate off the methanol virtually quantitatively, though it always still contains some methyl formate. Since the methanol is recycled to the synthesis stage and the methyl formate does not interfere with the latter, it is overall more economical to separate off mixtures of methanol and about 5–20% by weight of methyl formate. A fractionation section with 10–25 theoretical plates suffices for this purpose.

The fractionation section can be of any desired construction, ie. a bubble-cap tray column, valve-tray column, perforated tray column or packed column.

The purpose of the extraction section (4) of the column is to extract the formic acid from the reaction mixture in accordance with process feature (b), and at the same time to dehydrate it substantially or completely, in accordance with process feature (c), the water being returned to the hydrolysis section of the column. About 10 theoretical plates are necessary for complete dehydration. This number falls to about 5–8 if the acid required is only 85–95% strength by weight aqueous acid; such an acid in most cases satisfies the technical and economic requirements. As regards the construction of the column, the remarks made in connection with the fractionation section (6) apply here also.

Suitable extractants I, to be used in accordance with process feature (b), are particularly those carboxylic acid amides, conforming to the general definition, where $R^1$ and $R^2$ are identical alkyl of 3–6 carbon atoms or are cyclohexyl, and $R^3$ is hydrogen, methyl or ethyl. Examples of such carboxylic acid amides are di-n-butylformamide, di-n-pentylformamide, di-iso-pentylformamide, dicyclohexylformamide, di-n-butylacetamide and di-n-butylpropionamide. Amongst these, di-n-butylformamide has proved particularly suitable.

Since the carboxylic acid amides I, being weakly basic, form hydrogen bridge adducts with formic acid, they are advantageously used in such amount that when they circulate in the hydrolysis section (5) of the column (1) they are available in at least equimolar amount, based on the formic acid to be extracted. However, an excess of 0.1–1 mole is preferred. On the other hand, a less than equimolar amount (down to 0.5 mole of I per mole of formic acid to be extracted) can also be used, since the carboxylic acid amide is capable of extracting larger than stoichiometric amounts of formic acid.

Process step (e) serves to complete the procedure according to the invention, but is not itself part of the invention. This step may therefore be carried out in a conventional manner and does not require more detailed comment. The distillation in step (e) gives formic acid containing an amount of water corresponding to the water content of the carboxylic acid amide/formic acid/water mixture used as the feed.

The advantageous embodiment of the process of the invention which includes the additional feature (f) meets the general duty to minimize the energy consumption of any industrial process, even though higher capital costs may be incurred.

In the method of the invention, a substantial portion of the energy is used to evaporate the water in the extraction section of the column in order to recover an anhydrous or substantially anhydrous mixture of formic acid and extractant I and force the water back to the hydrolysis section. It is a specific object of the invention to reduce the amount of energy required.

This object is achieved by partially dehydrating the liquid aqueous formic acid, which collects in the lower zone of the hydrolysis section of the column, by a method of liquid-liquid extraction, before it enters the extraction section of the column. This means that the aqueous formic acid entering the extraction section of the column contains less water and the energy needed to evaporate the water is accordingly less.

Figure 2:
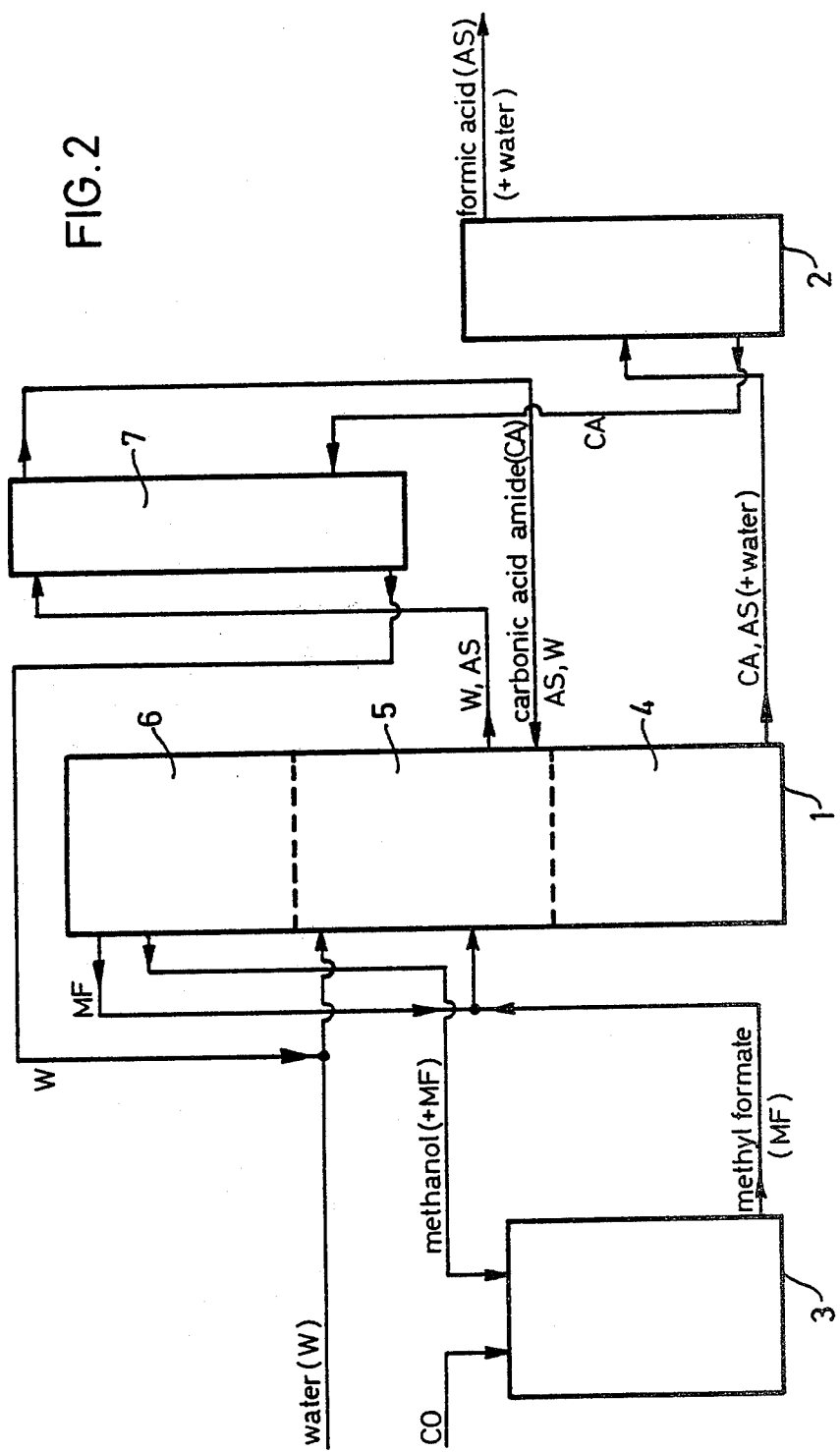

The arrangement of apparatus used in this embodiment, which essentially differs from the basic process of FIG. 1 only in the use of an additional extraction column (7), is illustrated in FIG. 2.

The aqueous formic acid is taken off the hydrolysis section (5) of the column at least one tray below the methyl formate feed point and fed to the extraction column (7) in which it is extracted countercurrent to the extractant I. Because the extractant circulation is operated as a closed system, the extractant obviously originates from distillation column 2. The extract phase obtained in (7) contains substantially the entire formic acid, the entire extractant and some of the water. This phase, which is low in water, is then returned to the hydrolysis section (5) of the column at least one tray below the outlet for aqueous formic acid. The raffinate phase from (7) consists substantially of water and is expediently returned to the hydrolysis section (5) of the column instead of a corresponding amount of fresh water.

The extraction column (7) can be of any desired construction and preferably has from 5 to 12 theoretical plates. The extraction as such may be carried out in a conventional manner and does not require more detailed comment.

The energy consumption of the process comprising the additional feature (f) is about 40% less than for the process defined by features (a) to (e). This saving will in most cases justify the extra investment.

The process according to the invention, characterized by features (a) to (e), is technologically notable because, apart from the formic acid column (2), it is carried out in a simple and technically elegant manner in a single apparatus, namely column 1, comprising the three sections (4), (5) and (6), even though this column must perform very diverse functions. The benefits thus achievable also accrue in the special embodiment defined by feature (f), even though this embodiment requires an additional extraction column.

EXAMPLE 1

An experimental column of 400 cm height and 5 cm diameter, of which the lower section (extraction section) was a packed column with 12 theoretical plates, the middle section (hydrolysis section) was a bubble-cap tray column with 12 trays and the upper section (fractionation section) was again a packed column with 21 theoretical plates, was operated under atmospheric pressure and after reaching steady-state operation was fed, at the level of the 12th tray of the hydrolysis section, with 180 g (10 moles) of water per hour, at 25° C., and at the level of the 1st tray of this section with 500 g (8.3 moles) of fresh methyl formate per hour.

At the level of the 14th plate of the fractionation section, 251 g of methanol and 29 g of methyl formate were taken off per hour, at 58° C. The remaining methyl formate (1,300 g per hour) and some methanol were recycled, after condensation, to the column together with the fresh methyl formate. Per hour, 940 g (6 moles) of di-n-butylformamide were added at the level of the 1st tray of the hydrolysis section, where the temperature was 90° C.

At the bottom of the column (at 170° C.), a mixture comprising 940 g of di-n-butylformamide, 362 g (7.9 moles) of formic acid and 40 g of water per hour was obtained. Distillation of this mixture in a downstream column under 70 mbar gave about 400 g per hour of 90% strength by weight aqueous formic acid together with virtually the entire amount of the di-n-butylformamide, which was recycled.

The mean residence time of all the reactants was about 15 minutes, of which about 13 minutes were attributable to the residence time in the hydrolysis section of the column. The heat input was effected via a thin film evaporator and was such as to give a reflux ratio of 3–3.5 at the top of the column.

If the energy input was increased to correspond to a reflux ratio of 4–4.5 and at the same time the water input was reduced, the extract phase was dehydrated more effectively and a 95% strength by weight acid was obtained.

EXAMPLE 2

An experimental column of 450 cm height and 5 cm diameter, of which the lower section (extraction section) was a packed column with 8 theoretical plates, the middle section (hydrolysis section) was a bubble-cap tray column with 25 trays and the upper section (fractionation section) was again a packed column with 22 theoretical plates, was operated under atmospheric pressure and after reaching steady-state operation was fed, at the level of the 25th tray of the hydrolysis section, with 145 g of fresh water and 1170 g of recycled water from the liquid-liquid extraction described below, and at the level of the 6th tray of the hydrolysis section with 454 g of fresh methyl formate and 1364 g of methyl formate from the fractionation section of the column which contained 60 g of methanol.

At the level of the 15th plate of the fractionation section, a mixture of 228 g of methanol and 26 g of methyl formate was taken off per hour and returned to the synthesis stage.

At the level of the 2nd bubble-cap tray of the hydrolysis section of the column, 2000 g/h of aqueous formic acid were taken off and fed to the top of a rotary-disk extraction column having 7 theoretical plates. This aqueous acid was extracted at 75° C. countercurrent to 2000 g/h of di-n-butylformamide. The water obtained in the extraction as the raffinate phase was returned, as mentioned above, together with fresh water to the hydrolysis section of the column, and the raffinate phase was also returned to the hydrolysis section at the level of the first tray.

At the bottom of the extraction section (at 170° C.) a mixture comprising 350 g of formic acid, 17 g of water and 2000 g of extractant was obtained per hour, which was treated in the manner described in Example 1 in the formic acid column to give 95% formic acid, the extractant obtained at the bottom being recycled to the extraction column.

As compared with the method of Example 1, the energy saving was about 40%.

We claim:

1. A process for producing anhydrous or substantially anhydrous formic acid by hydrolysis of methyl formate in a single column having an upper fractionating section, a middle hydrolysis section and a lower extraction section which comprises:

(a) passing water and methyl formate in countercurrent in the middle section of the column, wherein the methyl formate is hydrolyzed, (b) contacting the resulting formic acid in the lower section of the column with a carboxylic acid amide of the general formula I

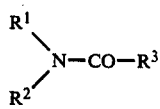   I where $R^1$ and $R^2$ are alkyl, which may also be linked to form a 5-membered or 6-membered ring, or are cyclohexyl, and $R^3$ is hydrogen or $C_1$–$C_4$-alkyl, the sum of the carbon atoms in radicals $R^1$, $R^2$ and $R^3$ being from 7 to 14, the carboxylic acid amide being fed into the lower end of the middle section of the column, whereby the formic acid is extracted, (c) distillatively dehydrating or substantially dehydrating the extract phase, consisting in the main of formic acid and the carboxylic acid amide in the lower section of the column, (d) removing the methanol and unconverted methyl formate by fractional distillation in the upper section of the column and (e) passing the anhydrous or substantially anhydrous extract phase to a second column where the extract phase is distilled to form the pure formic acid or concentrated aqueous formic acid leaving the carboxylic acid amide.

2. The process of claim 1, which includes the additional step of (f) passing the aqueous formic acid collecting in liquid form in the lower zone of the middle section of the column below the methyl formate feed point to a separate extraction column in which it is partly dehydrated by means of carboxylic acid amide I by the method of liquid-liquid extraction, returning the water thus obtained as the raffinate phase to the upper zone of the middle section of the column, and returning the extract phase comprising the formic acid, the extractant and some of the water supplied to the extraction column to the lower zone of the middle section of the column below the outlet for aqueous formic acid.

3. The process of claim 1 or 2, wherein the lower column section comprises 5 to 20 theoretical trays, the middle section comprises 1 to 20 theoretical trays and the upper section comprises 10 to 40 theoretical trays.

4. The process of claims 1 or 2, wherein the middle section of the column, in which the hydrolysis takes place, is a bubble-cap tray column.

5. The process of claim 1 or 2, wherein di-n-butylformamide is used as the extractant.

* * * * *